United States Patent

Szymanski et al.

US005733840A

[11] Patent Number: 5,733,840
[45] Date of Patent: *Mar. 31, 1998

[54] CATALYST CARRIER

[75] Inventors: Thomas Szymanski, Hudson, Ohio; John Lockemeyer, Sugarland, Tex.

[73] Assignee: Norton Chemical Process Products Corporation, Stow, Ohio

[*] Notice: The term of this patent shall not extend beyond the expiration date of Pat. No. 5,512,530.

[21] Appl. No.: 659,475

[22] Filed: Jun. 6, 1996

[51] Int. Cl.⁶ .................. B01J 21/00; B01J 21/04
[52] U.S. Cl. .................. 502/351; 502/439
[58] Field of Search .................. 502/350, 351, 502/439

[56] References Cited

U.S. PATENT DOCUMENTS

| 5,380,697 | 1/1995 | Matusz et al. | 502/348 |
| 5,384,302 | 1/1995 | Gerdes et al. | 502/439 |
| 5,512,530 | 4/1996 | Gerdes et al. | 502/351 |

Primary Examiner—Glenn Caldarola
Assistant Examiner—Alexander G. Ghyka
Attorney, Agent, or Firm—David Bennett

[57] ABSTRACT

A process for the production of an alumina based catalyst carrier in which a fired carrier body is impregnated with a source of titania in a liquid medium that upon heating yields titania and then calcined to generate titania uniformly dispersed in the carrier in an amount up to about 10% by weight.

9 Claims, No Drawings

CATALYST CARRIER

This invention relates to catalyst carriers and specifically to catalyst carriers based on ceramic components such as alumina that may be used as supports for metal and metal oxide catalyst components of use in a variety of chemical reactions.

BACKGROUND OF THE INVENTION

The use of ceramic based carriers and specifically alumina based catalyst carriers has previously been described in a number of patents including U.S. Pat. Nos. 5,100,859; 5,055,442; 5,037,794; and 4,874,739. Such carriers have a wide variety of potential applications in the catalytic field and are especially useful where the alumina base is alpha alumina.

A catalyst support needs to possess, in combination, at least a minimum surface area on which the catalytic component may be deposited, high water absorption and crush strength. The problem is that usually an increase in one can mean a reduction in another property. Thus high crush strength may mean low porosity. Often the balance is achieved by trial and error making the catalyst carrier art even more unpredictable than other chemical process art.

Carriers based on alpha alumina have an excellent balance of crush strength, abrasion resistance, porosity and catalytic performance that make them ideal for a range of catalytic applications. It has been found that the physical properties can be improved by incorporating a titania component into the mixture fired to produce the carrier. While such titania modification has been found to greatly improve the physical properties such as crush strength and abrasion resistance, it has been found that it does tend to affect the densification of the carrier structure and this can lead to unacceptable properties. This problem increases with increasing concentration of added titania. There is therefore a substantial advantage in the provision of a process for the incorporation of the highly beneficial titania component without causing such densification.

DESCRIPTION OF THE INVENTION

The present invention provides an advance over the disclosure in application Ser. No. 08/118,487 (U.S. Pat. No. 5,384,302) in that it teaches the advantages of addition of the titania component by an impregnation of the fired porous carrier prior to deposition of a catalyst on the carrier.

More specifically the invention provides a process for the production of an alpha alumina based catalyst carrier which comprises:

a) forming a mixture comprising alumina components, ceramic bond, a liquid medium and optionally, organic burnout materials, shaping aids and lubricants;

b) shaping the mixture into carrier bodies;

c) drying and firing the bodies at a temperature of from about 1200° to 1500° C. to form a porous carrier bodies;

d) impregnating the porous carrier bodies with a titania generator in a liquid medium; and then e) firing the impregnated bodies at a temperature sufficient to remove volatiles and generate titania.

In the discussion that follows the invention will be discussed in terms of added "titania" because, after the firing operation, it is assumed for the purposes of this Application that the titanium remaining in the carrier will be in the form of an oxide.

Since titania is not soluble in water it must be carried in to the pores of the fired porous carrier in solution or sol form. It should be understood therefore that any suitable soluble salt of titanium can be used provided that it decomposes to the oxide and leaves no residue or evolves no components that could interfere with the activity or performance of the catalyst deposited on the carrier. Thus titanyl oxalate, titanium (IV) bis(ammonium lactato) dihydroxide, or similar organic salts are suitable. In addition titania sols or slurries of heat-decomposable titanium compounds are usable providing they are fluid enough to penetrate the pores of the carrier. It is also possible to use a titanium alkoxide or other organometallic compound in a suitable liquid vehicle.

In the context of this Specification, the term "titania generator" is understood to embrace all such suitable salt solutions, slurries and sols that, under the conditions under which the carrier is produced, form titania.

Generally the use of a titanyl salt as the titania generator is preferred and the oxalate or dihydroxy bis-lactate are the most preferred titanium salts because they are very soluble and because they decompose at relatively low temperatures of from around 200°–320° C. Upon decomposition, an amorphous titania phase is formed which generally has too high a surface area for optimum results. It is preferred to calcine the impregnated carrier at a temperature at or above about 450°–500° C. at which the anatase form is generated. Heating at higher temperatures above about 773° C. generates the rutile form. Neither of these consequences is disastrous, especially if a larger amount of titania towards the upper end of the preferred range is used, but it must be observed that prolonged exposure to higher temperatures can lead to the titania sintering and forming larger crystals. This in general is not desirable. It is therefore desirable to calcine the impregnated carrier at a temperature from about 450°to 700° C., and more preferably from about 500°to 600° C. and for a time of from 15 to 120 minutes and preferably from about 30 to 60 minutes.

It is often found advantageous to add the titania generator in an amount that represents from about 0.05 to about 10%, and more preferably from about 0.1 to about 2.0% of the weight of the fired carrier, (calculated as $TiO_2$). Generally little selectivity advantage is seen as a result of incorporating more than about 0.5% of titania. Impregnation is preferably done by immersing the carrier particles in a titania generator which is then decomposed to titania when the carrier particles are fired.

The firing of the impregnated carrier is carried out under conditions adapted to generate titania. In the presence of alumina, the firing can result in the formation of aluminum titanate and this is in general less preferred than titania.

Certain forms of alumina and bond material may also contain titania as impurities or components. The contribution of such forms of titania are not included in the amounts specified above.

The carrier is heated at a temperature that is high enough to sinter the alumina particles and produce a structure with physical properties adequate to withstand the environment in which it is expected to operate. In practice temperatures of about 1200°–1500° C. and particularly 1300°–1500° C. are used to perform this sintering, (lower temperatures usually require longer times to achieve the same degree of sintering as higher temperatures). This may be done before or after the impregnation or if desired, at the time the catalyst components are placed on the carrier. Sintering before impregnation is generally the most preferred option.

The preferred catalyst carrier of the invention may comprise a number of alpha alumina components chosen to contribute to the desired physical properties, including porosity, pore volume, crush strength and the like. Often a combination of two different alpha aluminas is preferred, one component having larger particles mixed with a second component having smaller particles, in weight ratios of from about 10:90 to 90:10. The objective of this is to end up with a surface area, (in this document a reference to "surface area" is understood to mean the BET surface area measured using nitrogen or krypton as the adsorbed gas), in the finished product of from about 0.4 to about 5 $m^2/gm$. The surface area in the finished carrier is somewhat less than for the free alumina particles. Thus a convenient mixture may comprise for example, two types of alpha alumina particles, the first having a surface area of about 1 $m^2/gm$ and the second having a surface area of about 3 to 5 $m^2/gm$.

Part of the alpha alumina may be formed in situ from a precursor which is preferably boehmite. Good results are also obtained if the precursor comprises a mixture of boehmite with an aluminum trihydrate such as gibbsite or bayerite. Where such a mixture is used it is often preferred to use a weight ratio of the monohydrate, (boehmite), to trihydrate of from about 1:10 to about 1:3 and more preferably from about 1:8 to about 1:4. It is often preferred that, when a sol is formed from the precursor by addition of water, a submicron particle sized seed material is also added. This has the effect of reducing the temperature at which the transition to alpha alumina occurs and reduces the crystal size of the alpha alumina produced upon transformation. The seed used can be any material that is effective to produce nucleation sites in the precursor so as to reduce the transition temperature at which a transition alumina converts to alpha alumina. Seeds that accomplish this goal generally have the same crystal lattice type as alpha alumina itself and lattice dimensions that do not differ by too much from those of alpha alumina. Clearly the most convenient seed is alpha alumina itself and sub-micron sized particles of alpha alumina are the preferred seed. It is however possible to use other seeds such as alpha ferric oxide and chromium oxide.

Alpha alumina formed from the preferred seeded precursor when the extruded mixture is fired generally has a much finer crystal size than the alpha alumina particles with which the seeded precursor is mixed unless, during firing, it is maintained at a high temperature for a prolonged period. As produced, the seeded sol-gel material has a sub-micron crystal structure but if it is held at temperatures over 1400° C. for extended periods, crystal growth begins and the size differentiation may become less apparent.

The carrier of the invention preferably has a porosity of at least 50% and more desirably from about 60 to about 75%. The porosity is related to the surface area which is preferably from about 0.4 to about 5, and more preferably from about 0.6 to about 1.2 square meters/gram. The porosity may be obtained by addition of organic burnout material such as ground walnut shells or solid particles of a combustible hydrocarbon. Porosity may also be obtained without the use of burnout material by choice of particle sizes of the ceramic components sintered together to form the carrier.

It is usually preferred to add a ceramic bond material to the mixture from which the carrier is to be made to give added strength to the fired carrier. Conventional ceramic bond materials can be used and after firing these typically comprise components, (expressed as the oxides), such as silica, alumina, alkaline earth metal oxides, alkali metal oxides, iron oxide and titanium oxide, with the first two being the dominant components. It is found that bond materials containing significant amounts of alkali metals, that is up to about 5% and more preferably from about 2 to 4% are particularly suitable. Particularly suitable bond materials include calcium silicate and magnesium silicate either added as such or formed in situ.

DESCRIPTION OF PREFERRED EMBODIMENTS

The invention is further described with reference to the following examples which are for the purposes of illustration only and are not intended to imply any necessary limitation on the essential scope of the invention.

EXAMPLE 1

This Example details the preparation of the carriers made using the formulations described in the following Examples.

The ceramic components are mixed with a burn-out material, (walnut shell flour), and boric acid for about a minute. Water and an alpha alumina seed component are added, the water being in an amount that is necessary to make the mixture extrudable. Generally this is about 30% by weight. The mixture is mixed for about 4.5 minutes and then about 5% by weight based on the weight of the ceramic components, of vaseline is added as an extrusion aid. The mixture is then mixed for a further 3.5 minutes before being extruded in the form of hollow cylinders and dried to remove essentially all bound water. These were then fired in a tunnel kiln with a maximum temperature of about 1460°–1490° C. for about 5 hours.

The ingredients mixed were as follows:
Ceramic Components

| Alpha Alumina (Type #1) | 46.7% |
| Alpha Alumina (Type #2) | 27.4% |
| Alpha Alumina Seed (Type #3) | 2.2% |
| Gibbsite | 18.3% |
| Dispersible Boehmite | 4.1% |
| Ceramic Bond | 1.3% |

Other components expressed as percentage of the total ceramic components

| Organic Burnout (ground walnut shells) | 20% |
| Petroleum Jelly Lubricant | 5% |
| Boric Acid | 0.15% |
| Water sufficient to make extrudable | about 30% |

| Alumina | Type #1 | Type #2 | Type #3 | Gibbsite |
|---|---|---|---|---|
| med. part. size | 3.0–3.4µ | 4.0–8.0µ | <1.0µ | 4.0–20µ |
| crystallite size | 1.6–2.2µ | 3.0–4.0µ | — | — |
| $Na_2O$ content (%) | 0.02–0.06 | 0.1–0.3 | — | 0.1–0.3 |
| Surface Area | — | — | 10–135 $m^2/g$ | — |

The ceramic bond has, (in % by wt.), a typical composition of:

| $SiO_2$ | $Al_2O_3$ | $Fe_2O_3$ | $TiO_2$ | CaO | MgO | $Na_2O$ | $K_2O$ |
|---|---|---|---|---|---|---|---|
| 61.3 | 28.6 | 0.85 | 0.68 | 2.92 | 1.79 | 1.15 | 2.67 |

Impregnation of Carrier

The fired catalyst was divided into two and one portion was then impregnated with a titania-generating material in an amount sufficient to give a final titanium content in the dried and finished carrier in the desired amount. The other portion was given no titania treatment at all.

The impregnation was carried out by weighing out a suitable source of titanium in an amount necessary to give the desired level in the final carrier. In Example 1 this was in the form of a water-soluble titanium salt, (titanium (IV) bis(ammonium lactato) dihydroxide) commercially available as "TYZOR LA".

The total volume of solution used was in each case equivalent to the total pore volume of the carrier.

The carrier is impregnated by slow addition to the carrier in pellet form with agitation. When addition is complete, the impregnated carrier is allowed to stand for 30 minutes and then dried overnight at 120° C. It was then calcined 500° C. for six hours except where otherwise specified.

Catalyst Preparation

The carriers described above were used to prepare an ethylene oxide catalyst. The preparation method was generally as described in U.S. Pat. No. 5,380,697. Each of the carrier samples described above was given an identical treatment.

The Process

The following describes the standard microreactor catalyst test conditions and procedures used to test catalysts for the production of ethylene oxide from ethylene and oxygen.

Three to five grams of crushed catalyst (14–20 mesh) are loaded into a 0.21 inch inside diameter stainless steel U-shaped tube. The U tube is immersed in a molten metal bath (heat medium) and the ends are connected to a gas flow system. The weight of catalyst used and the inlet gas flow rate are adjusted to achieve a gas hourly space velocity of 6800 cc of gas per cc of catalyst per hour. The inlet gas pressure is 325 psig.

The gas mixture passed through the catalyst bed (in once-through operation) during the entire test run (including startup) consists of 25% ethylene, 7.0% oxygen, 7% carbon dioxide, 61% nitrogen, and 2.5 to 10 ppmv ethyl chloride as a moderator.

The reactor (heat medium) temperature is taken up 180° C. over a half hour period and then up to 190° C. and the 200° C. in successive half hour periods. Thereafter it was ramped up at 10° C. per hour for the next two hours followed by a further half hour to reach the operating temperature of 225° C. The temperature is then adjusted so as to achieve a constant ethylene oxide level in the product stream of 1.5% ($T_{1.5}$).

The moderator level is maintained at 10 ppmv for 6.5 hours and thereafter at 2. Due to slight differences in feed gas composition, gas flow rates, and the calibration of analytical instruments used to determine the feed and product gas compositions, the measured selectivity and activity of a given catalyst may vary slightly from one test run to the next.

To allow meaningful comparison of the performance of catalysts tested at different times, the catalysts described in this illustrative embodiment were tested simultaneously, (i.e. in parallel). The results showed:

With titania the $S_{1.5}$ and $T_{1.5}$ values were 83.3% and 227° C. Without the titania treatment the corresponding values were 82.5% and 235° C. This indicates that impregnation is a very effective way of securing the advantages of incorporating titania into the carrier.

EXAMPLE 2

An additional carrier according to the invention along with a comparison carrier were produced and treated with a catalyst exactly as described in Example 1.

The carrier differed however in the composition which was as follows:

Ceramic Components

| | |
|---|---|
| Alpha Alumina (Type #4) | 74.5% |
| Alpha Alumina (Type #5) | 24.5% |
| Ceramic Bond | 1.0% |

Other components expressed as percentage of the total ceramic components

| | |
|---|---|
| Organic Burnout (ground walnut shells) | 25% |
| Petroleum Jelly Lubricant | 5% |
| Boric Acid | 0.1% |
| Water sufficient to make extrudable | about 30% |

| Alumina | Type #4 | Type #5 |
|---|---|---|
| med. part. size | 3.0–4.0µ | 2.5–3.7µ |
| crystallite size | 3.0–3.2 | 2.0–2.5µ |
| Na$_2$O content (%) | 0.02–0.03 | 0.08–0.10 |

The ceramic bond has, (in % by wt.), a typical composition of:

| SiO$_2$ | Al$_2$O$_3$ | Fe$_2$O$_3$ | TiO$_2$ | CaO | MgO | Na$_2$O | K$_2$O |
|---|---|---|---|---|---|---|---|
| 58.76 | 36.55 | 1.22 | 1.51 | 0.90 | 0.26 | 0.11 | 0.57 |

The fired catalyst was divided into two and one portion was then treated with an aqueous titanyl oxalate solution in the manner described above in an amount sufficient to give a final titanium content in the dried and finished carrier of 500 ppm. The other portion was given no titania treatment at all.

To allow meaningful comparison of the performance the catalysts described in this illustrative embodiment were tested simultaneously, (i.e. in parallel). The results showed: With Titania the $S_{1.5}$ and $T_{1.5}$ values were 82.5% and 232° C.

Without the titania treatment the corresponding values were 81.7% and 235° C.

EXAMPLE 3

In this Example, the effect of the firing conditions used to generate the titania in the carrier on the selectivity of the resultant catalyst, is evaluated. In each case the carrier was produced in the same way and the catalyst deposited thereon was the same. The selectivity evaluation was carried out in the manner described in Example 1. The carrier was produced in either 6 mm or 8 mm diameter particles and the amount of titanium added amounted to 0.05% by weight in each case.

The results are set forth in Table 1 below.

TABLE 1

| Calc. Time | 8 mm Calc. Temp. (°C.) | | | | 6 mm Calc. Temp. (°C.) | | |
|---|---|---|---|---|---|---|---|
| (min.) | 250 | 300 | 400 | 500 | 500 | 550 | 600 |
| 15 | — | 81.8 | 82.2 | — | — | — | — |
| 30 | — | — | 82.6 | 82.8 | — | 82.6 | 82.9 |
| 45 | — | — | — | — | 82.7 | 82.9 | 82.8 |

TABLE 1-continued

| Calc. Time (min.) | 8 mm Calc. Temp. (°C.) | | | | 6 mm Calc. Temp. (°C.) | | |
|---|---|---|---|---|---|---|---|
| | 250 | 300 | 400 | 500 | 500 | 550 | 600 |
| 60 | — | — | — | 82.9 | 82.5 | 83.0 | 82.8 |
| 360 | 58.4 | 83.0 | 82.9 | 83.3 | 83.3 | — | — |

As will be clear from the above data, the firing should preferably be at a temperature of about 300° C. or higher for a time that is at least 15 minutes and up to about 360 minutes or more, with higher temperatures allowing shorter times.

EXAMPLE 4

The following Example traces the effect of firing conditions on the selectivity in the manner described in Example 1 except that the selectivity was assessed with the conditions adjusted such that the conversion to ethylene oxide was maintained at 40% and the feed composition was as follows:

| Oxygen | 8.5 vol % |
|---|---|
| Ethylene | 30.0 vol % |
| Carbon Dioxide | 5.0 vol % |
| Nitrogen | 54.0 vol % |
| Ethyl Chloride | 2.5 ppmv | and a flow rate of 3300 GHSV at a pressure of 210 psig was maintained.

The figures quoted are therefore the $S_{40}$ and $T_{40}$ values. The impregnation was performed using the titanyl oxalate salt.

| Titanium Content (% by wt) | TEMPERATURE OF CALCINATION (°C.) | | | | | |
|---|---|---|---|---|---|---|
| | 250 | 500 | 750 | 1000 | 1250 | 1350 |
| 0.00 | 81.8 | — | 82.1 | — | — | — |
| | 231 | — | 229 | — | — | — |
| 0.05 | 80.9 | 82.4 | 82.0 | 81.8 | 81.6 | — |
| | 231 | 218 | 219 | 222 | 233 | — |
| 0.50 | — | 81.2 | 82.4 | 81.7 | 82.4 | — |
| | — | 226 | 222 | 220 | 221 | — |
| 1.00 | — | 76.4 | 79.1 | 82.1 | 82.6 | 82.5 |
| | — | 227 | 219 | 218 | 219 | 225 |
| 2.00 | — | 73.1 | 81.8 | 82.1 | 82.5 | 82.6 |
| | — | 230 | 219 | 220 | 219 | 220 |

The titania content can be obtained from the titanium content figures quoted above by multiplying be 1.67.

The above data suggest that firing at too high a temperature can be detrimental and longer times of firing, at temperatures above about 500° C., does not improve selectivity.

What is claimed is:

1. A process for the production of an alpha alumina based catalyst carrier which comprises:
   a) forming a mixture comprising alumina components, ceramic bond, an liquid medium and optionally, organic burnout materials, shaping aids and lubricants;
   b) shaping the mixture into carrier bodies;
   c) drying and firing the bodies at a temperature of from 1200° to 1500° C. to form a porous carrier bodies;
   d) impregnating the porous carrier bodies with titania generator in a liquid medium; and then
   e) firing the impregnated bodies at a temperature sufficient to remove volatiles and generate titania.

2. A process according to claim 1 in which the dried fired carrier body is impregnated using a titania generator selected from the group consisting of a titania sol and an aqueous solution of a titanium compound containing ligands that combust to volatile products leaving titania when the impregnated carrier is fired.

3. A process for the production of a catalyst carrier according to claim 1 in which at least 80% by weight of the alumina components is provided by alpha alumina.

4. A process according to claim 1 in which the titania generator is added by impregnation in a volume amount equal to the pre volume of the carrier and sufficient to provide form about 0.05 to about 10% by weight of the weight of the finished carrier.

5. A process according to claim 1 in which the impregnated carrier is calcined a temperature between 400° and 700° C.

6. A process according to claim 1 in which a ceramic bond material comprising silica, alumina and an alkali metal is added to the extrudable mixture in an amount that is from about 1 to about 3% of the weight of the alumina components, expressed as alpha alumina, in the mixture.

7. A process for the production of a catalyst carrier which comprises:
   a) forming a mixture comprising:
      i) an alpha alumina having a first component with a median particle size of from about 2 to about 4 microns and a second component with a median particle size of about 4 to about 8 microns;
      ii) a seeded, hydrated precursor of alpha alumina in an amount sufficient to provide from about 5 to about 60% by weight of the total weight of alpha alumina in the catalyst carrier product;
      iii) from about 0 to about 40%, based on the weight of the alpha alumina, of a burnout material;
      iv) from about 1 to about 3% based on the weight of alumina in the composition, expressed as alpha alumina, of a ceramic bond material comprising silica alumina and an alkali metal; and
      v) water in sufficient quantity to shape the above mixture;
   b) forming the mixture into the desired shape; and
   c) firing to convert the seeded precursor of alpha alumina to alpha alumina and form a porous carrier product in which alpha alumina particles with a median particle size of from about 3 to about 8 microns are dispersed in a matrix of alpha alumina derived from the seeded precursor material; and
   d) adding to the porous fired carrier a titania generator selected from the group consisting of an aqueous titania sol and an aqueous solution of a soluble titanium salt in an amount equivalent to a added titania content in the final carrier formulation of from about 0.05 to about 5% of the weight of the carrier; and
   e) firing the impregnated carrier to remove the water and generate the titania in the anatase form.

8. A process according to claim 7 in which the precursor of alpha alumina is seeded with a sub-micron sized particles of alpha alumina in an amount that is from about 0.2 to about 5% by weight based on the total alumina weight, measured as alpha alumina, in the catalyst carrier.

9. A process according to claim 7 in which the impregnated carrier is calcined at a temperature of from 400° to 700° C.

* * * * *